United States Patent
Breen et al.

(10) Patent No.: US 11,955,244 B2
(45) Date of Patent: Apr. 9, 2024

(54) GENERATING RISK DETERMINATION MACHINE LEARNING FRAMEWORKS USING PER-HORIZON HISTORICAL CLAIM SETS

(71) Applicant: Optum Services (Ireland) Limited, Dublin (IE)

(72) Inventors: Conor Breen, Dublin (IE); Lorcan B. MacManus, County Kildare (IE); Peter Cogan, Dublin (IE)

(73) Assignee: Optum Services (Ireland) Limited, Dublin (IE)

(*) Notice: Subject to any disclaimer, the term of this patent is extended or adjusted under 35 U.S.C. 154(b) by 445 days.

(21) Appl. No.: 17/305,273

(22) Filed: Jul. 2, 2021

(65) Prior Publication Data
US 2023/0005067 A1  Jan. 5, 2023

(51) Int. Cl.
| | |
|---|---|
| *G16H 50/30* | (2018.01) |
| *G06N 20/00* | (2019.01) |
| *G06Q 40/08* | (2012.01) |
| *G16H 10/60* | (2018.01) |
| *G16H 15/00* | (2018.01) |
| *G16H 50/20* | (2018.01) |
| *G16H 50/70* | (2018.01) |

(52) U.S. Cl.
CPC .............. *G16H 50/30* (2018.01); *G06N 20/00* (2019.01); *G06Q 40/08* (2013.01); *G16H 10/60* (2018.01); *G16H 15/00* (2018.01); *G16H 50/20* (2018.01); *G16H 50/70* (2018.01)

(58) Field of Classification Search
CPC .. G16H 10/00–80/00; G06Q 10/00–2250/905; G06N 3/00–99/007
See application file for complete search history.

(56) References Cited

U.S. PATENT DOCUMENTS

| | | |
|---|---|---|
| 8,515,777 B1 | 8/2013 | Rajasenan |
| 8,990,135 B2 | 3/2015 | Syed et al. |
| 9,224,180 B2 | 12/2015 | Macoviak et al. |
| 10,483,003 B1 | 11/2019 | McNair et al. |

(Continued)

FOREIGN PATENT DOCUMENTS

| | | | |
|---|---|---|---|
| CN | 108256720 A | * | 7/2018 |
| WO | 2019/046854 A1 | | 3/2019 |

OTHER PUBLICATIONS

Choi, Karmel W. et al. "Early Risk and Resiliency Factors Predict Chronic PTSD in Caregivers of Patients Admitted to a Neuroscience Intensive Care Unit," Critical Care Medicine, May 2018, vol. 46, No. 5, pp. 713-719, DOI: 10.1097/CCM.0000000000002988.

(Continued)

*Primary Examiner* — Jonathon A. Szumny
(74) *Attorney, Agent, or Firm* — Alston & Bird LLP

(57) ABSTRACT

There is a need for more accurate and more efficient predictive data analysis steps/operations. This need can be addressed by, for example, techniques for efficient predictive data analysis steps/operations. In one example, a method includes generating, by a processor, utilizing a risk determination machine learning model and based at least in part on one or more hidden features of the first predictive entity, the predicted risk measure, and performing one or more prediction-based actions based at least in part on the predicted risk measure.

20 Claims, 8 Drawing Sheets

(56) References Cited

U.S. PATENT DOCUMENTS

| | | | |
|---|---|---|---|
| 10,621,491 B2 | 4/2020 | Vallee | |
| 2016/0135706 A1 | 5/2016 | Sullivan et al. | |
| 2016/0171618 A1* | 6/2016 | Besman | G06Q 40/08 |
| | | | 705/4 |
| 2018/0144825 A1 | 5/2018 | Xu et al. | |
| 2018/0365772 A1* | 12/2018 | Thompson | G06N 7/01 |
| 2021/0342757 A1* | 11/2021 | Yu | G06N 7/01 |
| 2022/0005121 A1* | 1/2022 | Hayward | G06N 3/044 |
| 2022/0157435 A1* | 5/2022 | Wu | G16H 20/70 |
| 2022/0399132 A1* | 12/2022 | Shah | G06N 3/082 |

OTHER PUBLICATIONS

Schulz, Richard et al. "Long-Term Care Placement of Dementia Patients and Caregiver Health and Well-Being," The Journal of the American Medical Association, Aug. 25, 2004, vol. 292, No. 8, pp. 961-967.

\* cited by examiner

500

```
┌─────────────────────────────────────────────────┐
│ Determine a primary event for each candidate predictive entity │
│ of a plurality of candidate predictive entities │
│                       502                       │
└─────────────────────────────────────────────────┘
                         │
                         ▼
┌─────────────────────────────────────────────────┐
│ Determine a prediction time horizon for each candidate │
│ predictive entity based on the primary event associated with the │
│          candidate predictive entity            │
│                       504                       │
└─────────────────────────────────────────────────┘
                         │
                         ▼
┌─────────────────────────────────────────────────┐
│ Identify a ground-truth subset of the ground-truth predictive │
│                      entities                   │
│                       506                       │
└─────────────────────────────────────────────────┘
                         │
                         ▼
┌─────────────────────────────────────────────────┐
│ Determine ground-truth risk measure for each ground-truth │
│    predictive entity in the ground-truth subset │
│                       508                       │
└─────────────────────────────────────────────────┘
                         │
                         ▼
┌─────────────────────────────────────────────────┐
│ Train the risk determination machine learning model based on │
│ ground-truth risk measure for each ground-truth predictive │
│                      entity                     │
│                       510                       │
└─────────────────────────────────────────────────┘
```

FIG. 5

| MEMBER ID ▽ | Caregiver ID | Caregiver Notes | Caregiver Risk Score | Recommended Action |
|---|---|---|---|---|
| 234456789 | 397540097 | 45 Year Old Female With Hypertension | 35% | Click To Send Electronic Communication With Resources On Hypertension |
| 34567891 | 68939807 | 52 Year Old Male | 82% | Schedule Home Visit By July 5 |

CLICK TO SORT

GENERATING RISK DETERMINATION MACHINE LEARNING FRAMEWORKS USING PER-HORIZON HISTORICAL CLAIM SETS

BACKGROUND

Various embodiments of the present invention address technical challenges related to performing predictive data analysis steps/operations that are configured to determine predictive risk measures with respect to predictive entities and disclose various innovative techniques for improving efficiency and/or reliability of predictive data analysis systems.

BRIEF SUMMARY

In general, embodiments of the present invention provide methods, apparatuses, systems, computing devices, computing entities, and/or the like for performing predictive data analysis steps/operations that are configured to generate a predicted risk measure for a first predictive entity. In accordance with one aspect, a method for generating a predicted risk measure for a first predictive entity is provided. In one embodiment, the method comprises: generating, by a processor, and utilizing a risk determination machine learning model and based at least in part on one or more hidden features of the first predictive entity, the predicted risk measure, wherein: (i) the risk determination machine learning model is generated based at least in part on a ground-truth risk measure for each ground-truth predictive entity in a ground-truth subset of a plurality of candidate predictive entities, (ii) the first predictive entity is among the plurality of candidate predictive entities but is outside of the ground-truth subset, (iii) each ground-truth predictive entity is associated with a prediction time horizon and a per-horizon historical claim set within the prediction time horizon, (iv) each per-horizon claim count of a per-horizon claim set for a ground-truth predictive entity satisfies a per-horizon claim count threshold, (v) each prediction time horizon for a ground-truth predictive entity is determined based at least in part on a primary event associated with the ground-truth predictive entity, (vi) each primary event for a ground-truth predictive entity is determined based at least in part on a diagnosis timestamp for a recipient entity associated with the ground-truth predictive entity, and (vii) each ground-truth risk measure for a predictive entity is determined based at least in part on the per-horizon claim set for the ground-truth predictive entity; and performing, using the processor, one or more prediction-based actions based at least in part on the predicted risk measure.

In accordance with another aspect, an apparatus for generating a predicted risk measure for a first predictive entity is provided, the apparatus comprising at least one processor and at least one memory including program code, the at least one memory and the program code configured to, with the processor, cause the apparatus to at least: generate, using a risk determination machine learning model and based at least in part on one or more hidden features of the first predictive entity, the predicted risk measure, wherein: (i) the risk determination machine learning model is generated based at least in part on a ground-truth risk measure for each ground-truth predictive entity in a ground-truth subset of a plurality of candidate predictive entities, (ii) the first predictive entity is among the plurality of candidate predictive entities but is outside of the ground-truth subset, (iii) each ground-truth predictive entity is associated with a prediction time horizon and a per-horizon historical claim set within the prediction time horizon, (iv) each per-horizon claim count of a per-horizon claim set for a ground-truth predictive entity satisfies a per-horizon claim count threshold, (v) each prediction time horizon for a ground-truth predictive entity is determined based at least in part on a primary event associated with the ground-truth predictive entity, (vi) each primary event for a ground-truth predictive entity is determined based at least in part on a diagnosis timestamp for a recipient entity associated with the ground-truth predictive entity, and (vii) each ground-truth risk measure for a predictive entity is determined based at least in part on the per-horizon claim set for the ground-truth predictive entity; and perform one or more prediction-based actions based at least in part on the predicted risk measure.

In accordance with yet another aspect, a computer program product for generating a predicted risk measure for a first predictive entity is provided, the computer program product comprising at least one non-transitory computer-readable storage medium having computer-readable program code portions stored therein, the computer-readable program code portions configured to: generate, using a risk determination machine learning model and based at least in part on one or more hidden features of the first predictive entity, the predicted risk measure, wherein: (i) the risk determination machine learning model is generated based at least in part on a ground-truth risk measure for each ground-truth predictive entity in a ground-truth subset of a plurality of candidate predictive entities, (ii) the first predictive entity is among the plurality of candidate predictive entities but is outside of the ground-truth subset, (iii) each ground-truth predictive entity is associated with a prediction time horizon and a per-horizon historical claim set within the prediction time horizon, (iv) each per-horizon claim count of a per-horizon claim set for a ground-truth predictive entity satisfies a per-horizon claim count threshold, (v) each prediction time horizon for a ground-truth predictive entity is determined based at least in part on a primary event associated with the ground-truth predictive entity, (vi) each primary event for a ground-truth predictive entity is determined based at least in part on a diagnosis timestamp for a recipient entity associated with the ground-truth predictive entity, and (vii) each ground-truth risk measure for a predictive entity is determined based at least in part on the per-horizon claim set for the ground-truth predictive entity; and perform one or more prediction-based actions based at least in part on the predicted risk measure.

BRIEF DESCRIPTION OF THE DRAWINGS

Figure 1:
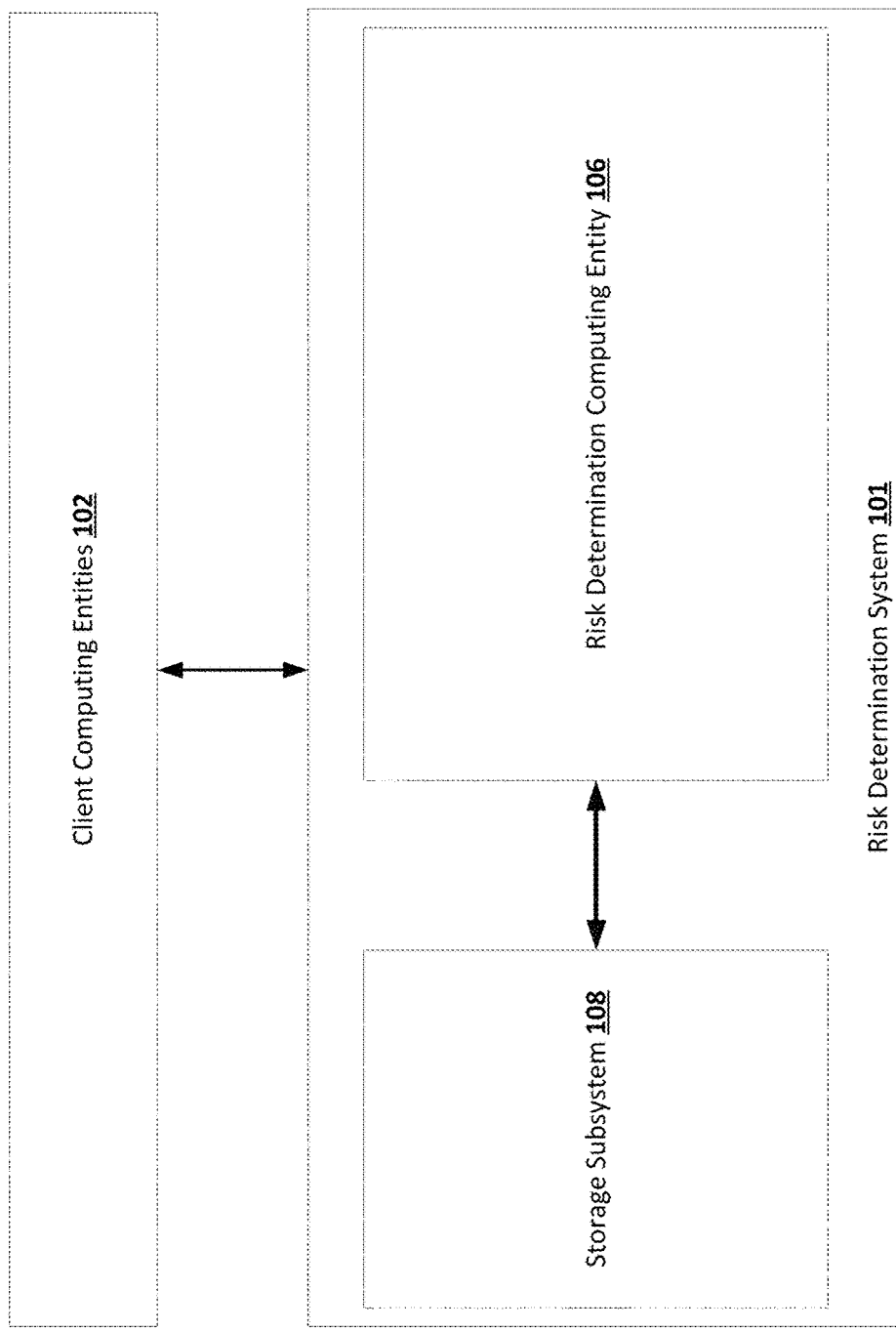
Figure 2:
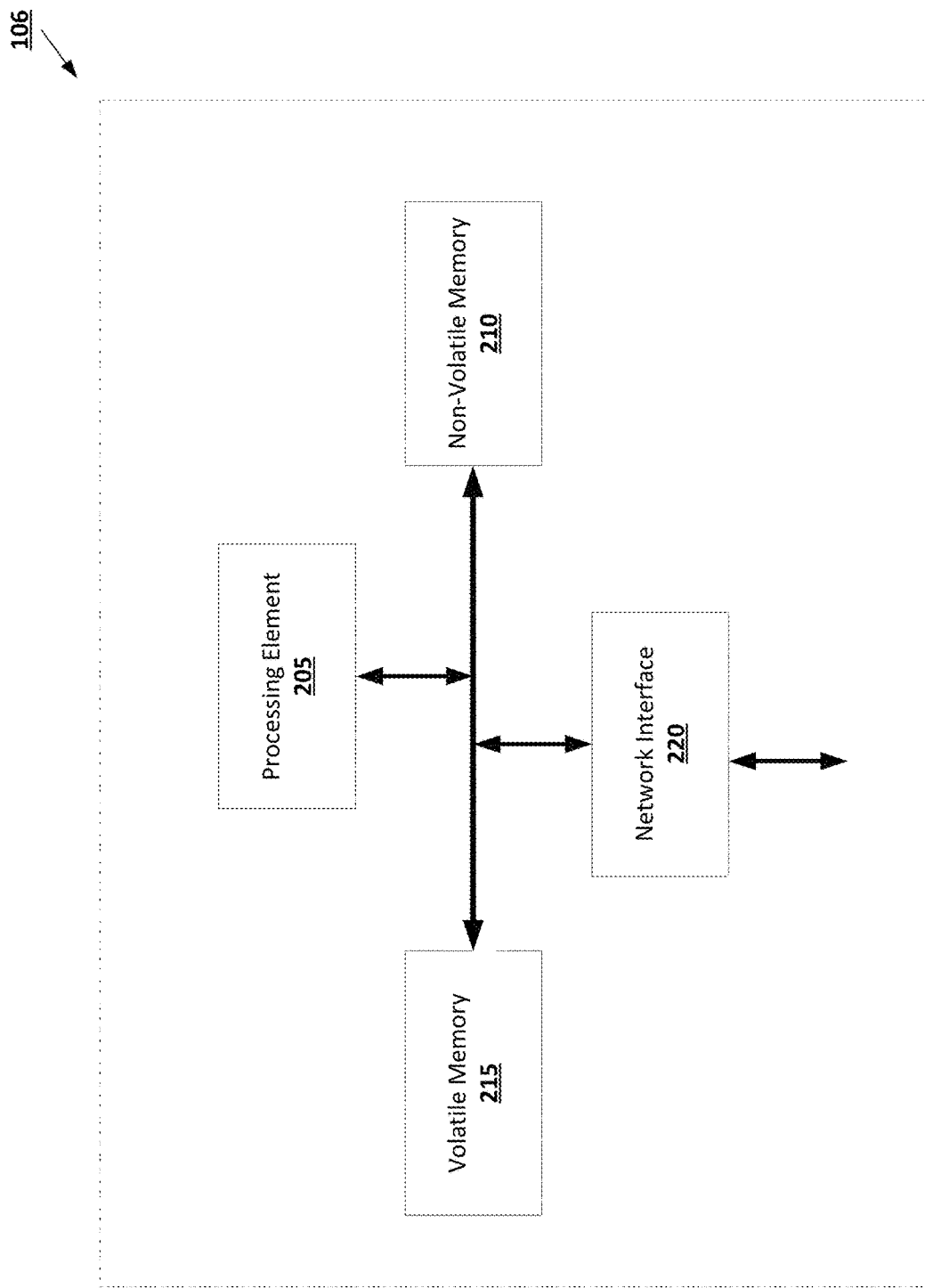
Figure 3:
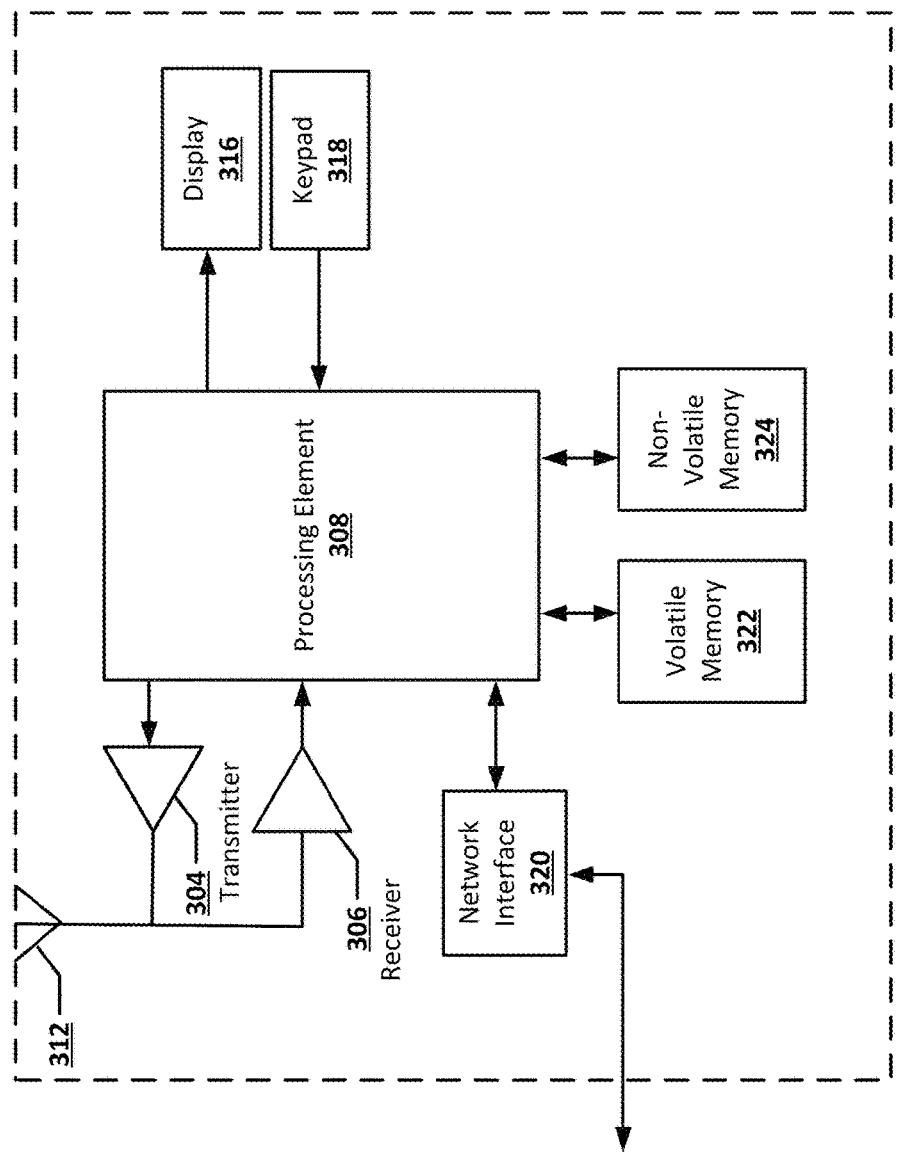
Figure 4:
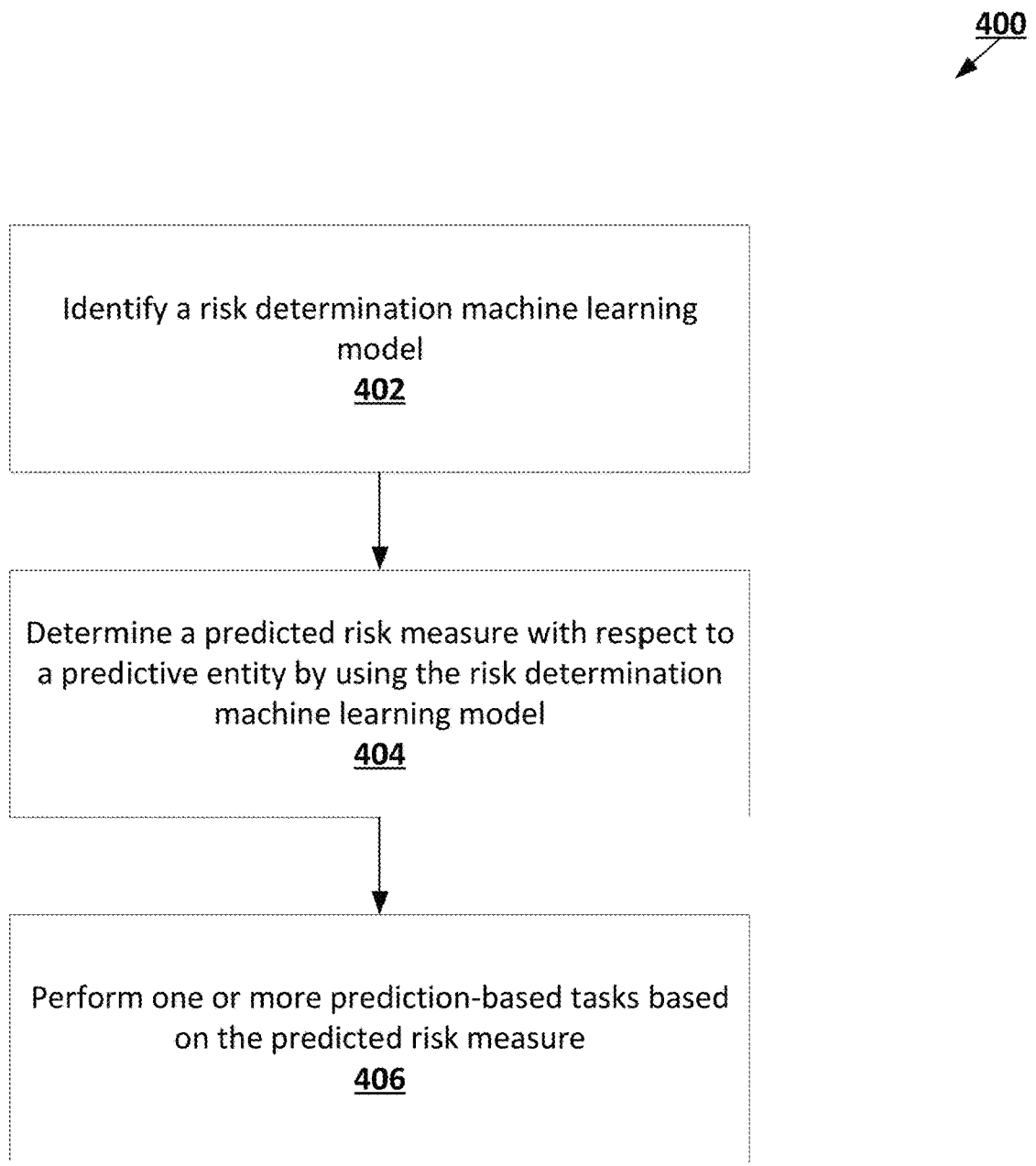
Figure 6:
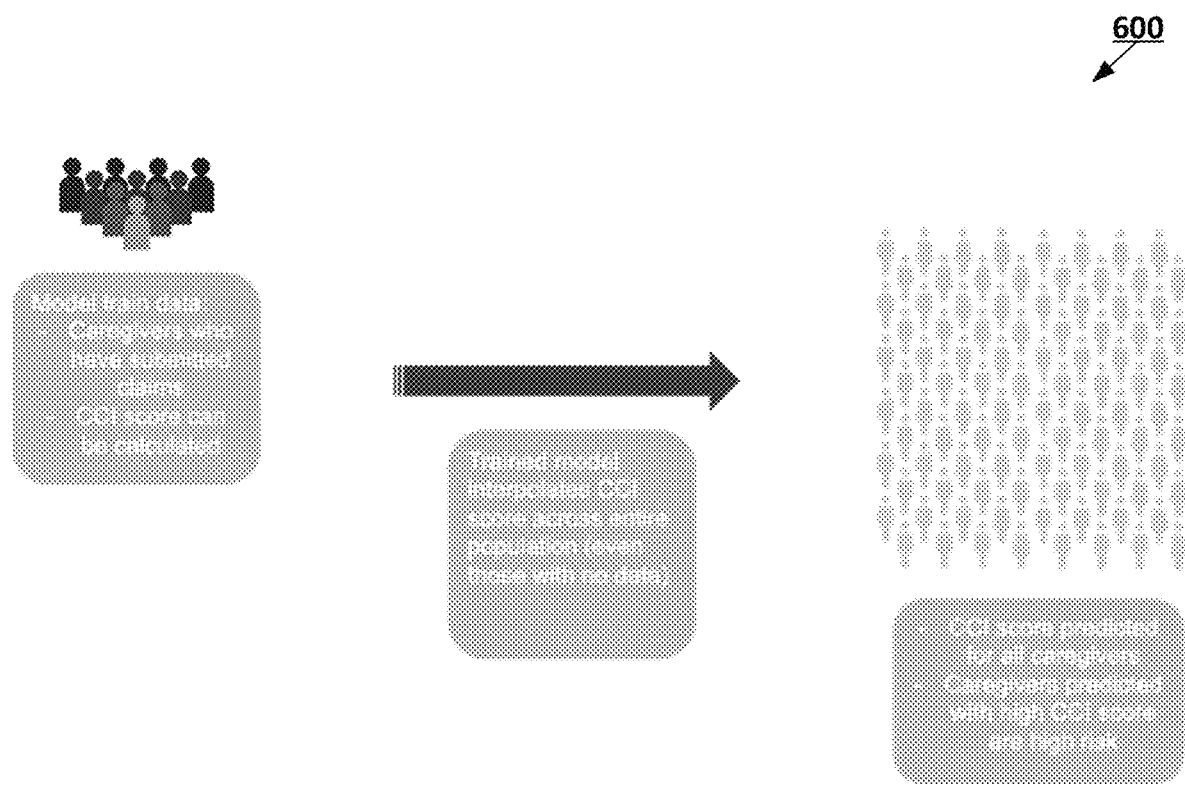
Figure 7:
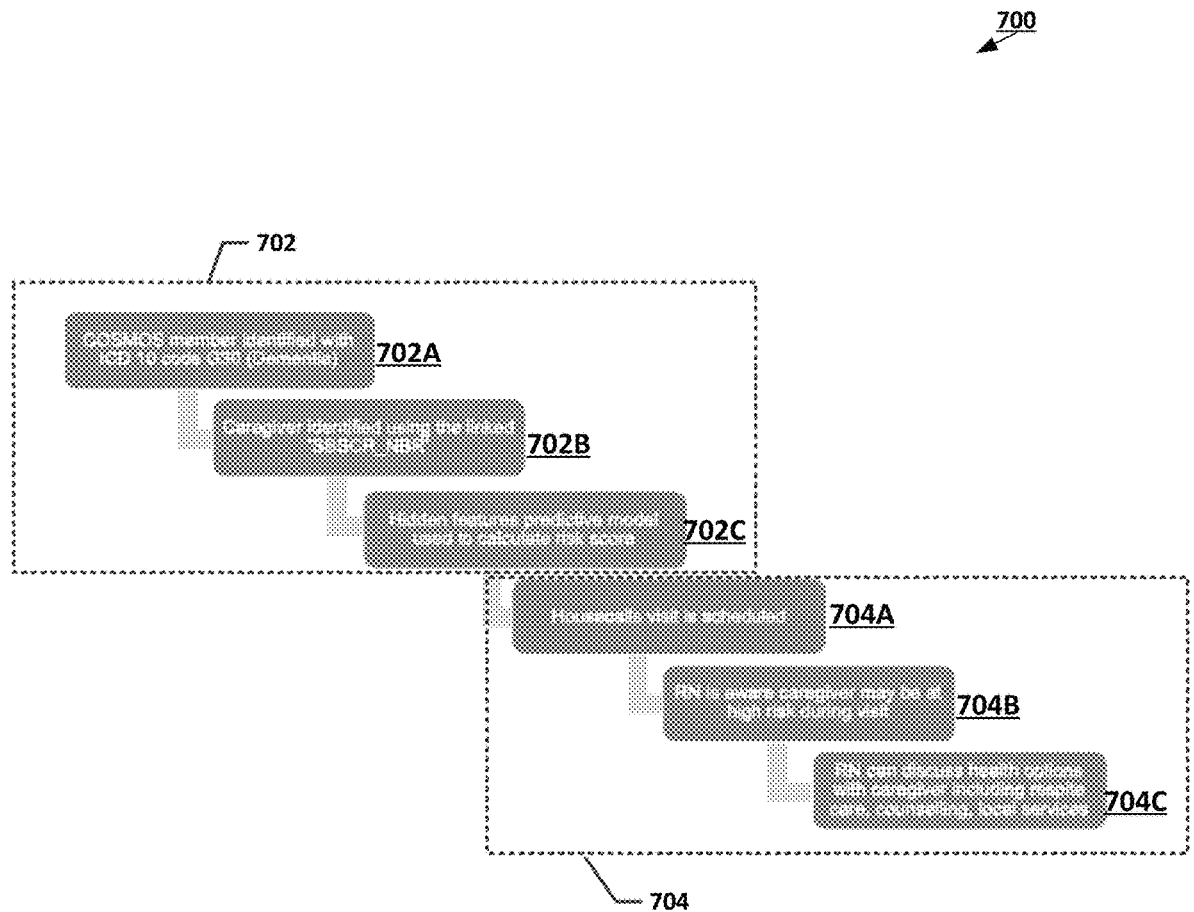

Having thus described the invention in general terms, reference will now be made to the accompanying drawings, which are not necessarily drawn to scale, and wherein:

FIG. 1 provides an exemplary overview of a system that can be used to practice embodiments of the present invention;

FIG. 2 provides an example predictive data analysis computing entity in accordance with some embodiments discussed herein;

FIG. 3 provides an example external computing entity in accordance with some embodiments discussed herein;

FIG. 4 provides a flowchart diagram of an example process for generating a predicted risk measure by a risk determination machine learning model in accordance with some embodiments discussed herein;

FIG. 5 provides a flowchart diagram of an example process for generating a risk determination machine learning model in accordance with some embodiments discussed herein;

FIG. 6 provides an operational example of generating a predicted risk measure in accordance with some embodiments discussed herein;

FIG. 7 provides an operational example configured to perform one or more prediction-based actions based at least in part on a predicted risk measure in accordance with some embodiments discussed herein; and FIG. 8 provides an operational example of a prediction output user interface in accordance with some embodiments discussed herein.

DETAILED DESCRIPTION

Various embodiments of the present invention are described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL ADVANTAGES

Various embodiments of the present invention disclose techniques for performing predictive data analysis steps/operations that are configured to generate a predicted risk measure for a predictive entity. These techniques are in turn configured to improve the efficiency of performing the noted predictive data analysis steps/operations and reliability of the generated results. Typically, predictive data analysis steps/operations require analysis of large amounts of data in order to accurately generate a predictive output. Accordingly, a predictive output may be inaccurate or unreliable in an instance in which insufficient amounts of data are available. Additionally, existing techniques are time consuming and require a lot of computational resources. There is a need for improved systems and methods that are configured to generate accurate predictive outputs in an efficient manner in an instance in which limited data and/or computing resources are available. Various embodiments of the present invention address that need by disclosing techniques for training risk determination machine learning models using per-horizon historical claim sets for ground-truth predictive entities whose per-horizon historical claim counts satisfy a per-horizon historical claim count threshold. The inventors have confirmed, via experiments and theoretical calculations, that various embodiments of the disclosed techniques improve efficiency and accuracy of predictive data analysis systems and predictive data analysis relative to various state-of-the-art solutions.

Moreover, various embodiments of the present invention address the challenge of computing a risk index for caregivers for whom there is no direct data (e.g., caregivers who are not submitting their own health claims with sufficient regularity) to provide a conventionally computed direct risk index. These caregivers may be at risk of serious adverse health outcomes and often fail to look after their own health due to their stressful circumstances. In contrast, the care recipients associated with these caregivers may have an abundance of indirect data relating to the caregivers' circumstances. A goal of various embodiments of the present invention is to generate and utilize a caregiver risk determination machine learning model that can be built using a subset of the data for which there is sufficient direct caregiver data and corresponding care recipient data. The model can then be used to make predictions about the health status of caregivers using as input the (abundant) care recipient data and some other known caregiver attributes. In this way, health risks in a population that is difficult to reach can be accurately predicted.

The predictive model at the heart of various embodiments of the present invention may be a supervised regression model which predicts a Charlson Comorbidity Index (CCI) score (typically used as a prediction tool for patients with comorbid conditions) of a caregiver over a time period of interest (e.g., two years). The data from the model is taken from the small pool of caregivers who have submitted sufficient claims during the two years after a diagnosis to compute a CCI score. These claims are then used to calculate the CCI score for these caregivers in the dataset. A supervised regression model is then built that will be able to interpolate a CCI across the entire population of caregivers in the cohort, even those who are not submitting any claims.

II. DEFINITIONS OF CERTAIN TERMS

The term "predictive entity" may refer to a data object that describes an entity with respect to which one or more predictive tasks/operations are performed. In some embodiments, a predictive entity may refer to a data object that describes a caregiver entity (e.g., a member, or the like). The caregiver entity may receive healthcare services or products (or any other type of service or product) rendered by a provider. The caregiver entity may be associated with a health insurance insurer and may be considered a member of a program associated with the health insurance insurer. An example predictive entity may correspond with an identifier (e.g., caregiver identifier such as member name, member ID and/or the like). The example caregiver entity may be associated with a recipient entity (e.g., care recipient entity) that is in turn associated with a primary event. In some embodiments the predictive entity (e.g., caregiver entity) may be one of a plurality of candidate predictive entities but may be outside a ground-truth subset of the plurality of candidate predictive entities.

The term "primary event" may refer to a data object that describes a record of an occurred event associated with a predictive entity. An example primary event may be determined based at least in part on a diagnosis timestamp for a care recipient entity. The care recipient entity may, in some examples, be associated with a caregiver entity. The primary event may comprise a primary event code defining one or more primary event attributes (e.g., medical claim attributes). The primary event may correspond with a care recipient entity diagnosis that is associated with an increased or increasing predicted risk measure for an associated predictive entity (e.g., caregiver entity) over a prediction time horizon. For example, the primary event may precipitate or lead to one or more medical claim entries, diagnoses and/or the like for a caregiver entity that is associated with the care recipient entity. In some embodiments, a medical claim entry may refer to a data object that describes a request for payment/reimbursement for services rendered, materials used, equipment provided, and/or the like (e.g., a claim or claim filing). In various embodiments, a claim may be a request for payment/reimbursement for a consultation with a primary care doctor, a medical procedure or an evaluation performed by a medical practitioner, a laboratory test performed by a laboratory, a surgery, durable medical equipment provided to an injured member, medications or other materials used in the treatment of a care recipient entity or caregiver entity, and/or the like.

The term "risk determination machine learning model" may refer to a data object that describes operations and/or parameters of a machine learning model that is configured to process hidden features of a predictive entity (e.g., caregiver entity) and generate a predicted risk measure for the predictive entity. In some embodiments, the risk determination machine learning model may be generated based at least in part on a ground-truth risk measure for each of a plurality of ground-truth predictive entities in a ground-truth subset of a plurality of candidate predictive entities. In some examples, each ground-truth risk measure is determined based at least in part on a Charlson Comorbidity Index (CCI) score for a per-horizon historical claim set associated with the ground-truth predictive entity. Each of the ground-truth subset of predictive entities may be associated with a primary event. An example of a risk determination machine learning model is a trained supervised machine learning model (e.g., a trained supervised regression model, a convolutional neural network model, and/or the like). In some embodiments, an example input to the risk determination machine learning model may be or comprise a multi-dimensional vector. Similarly, an example output from the risk determination machine learning model may be or comprise a multi-dimensional vector. In some embodiments, input features for the risk determination machine learning model may include hidden features (e.g., claim features such as count of claims, frequency of claims or the like), care recipient entity information/data (e.g., historical claim data), known caregiver entity data/information (e.g., demographic information such as age, gender, geographic location and/or the like), combinations thereof, and/or the like. The operations of the risk determination machine learning model may lead to performing one or more prediction-based actions or tasks.

The term "hidden features" may refer to a data object that describes one or more features/attributes associated with a predictive entity that are processed by a risk determination machine learning model in order to generate a predictive output (e.g., a predicted risk measure). Example hidden features may include member demographic information/data (e.g., age, gender, co-morbidities and/or the like), claim frequency, claim type, claim value/amounts (e.g., billed, paid and the like), number of hospitalizations, hospitalization time, duration of service, provider demographic information/data (e.g., specialty), diagnosis codes, procedure codes, facility, and/or the like.

The term "predicted risk measure" may refer to a data object that describes a predictive output representative of an inferred measure of risk with respect to a predictive entity. In some embodiments, the predicted risk measure may be or comprise a morbidity index defining an expected survival period for the predictive entity. An example predicted risk measure may be or comprise a Charlson Comorbidity Index (CCI) score. The example predicted risk measure may be generated using a risk determination machine learning model and based at least in part on one or more hidden features of the example predictive entity. The predicted risk measure may be used to perform one or more prediction-based actions with respect to the predictive entity.

The term "ground-truth predictive entity" may refer to a data object that describes a predictive entity that is associated with a per-horizon claim count that satisfies a per-horizon claim count threshold. For example, a ground-truth predictive entity may be a predictive entity having a number of claims within a defined prediction time horizon that satisfies a claim count threshold.

The term "ground-truth risk measure" may refer to a data object that describes a determined measure of risk with respect to a ground-truth predictive entity that is determined based at least in part on a per-horizon historical claim set for the ground-truth predictive entity. The per-horizon historical claim set may refer to a count of claims of a predictive entity (e.g., care recipient entity) occurring within a prediction time horizon that satisfies a predetermined threshold (e.g., a per-horizon claim count threshold). The example ground-truth risk measure may be determined based at least in part on a CCI score for the per-horizon historical claim set. In some embodiments, a plurality of ground-truth risk measures associated with a ground-truth subset of ground-truth predictive entities may be utilized to train a machine learning model (e.g., a risk determination machine learning model).

The term "prediction time horizon" may refer to a data object describing a defined-length time period following a primary event. The prediction time horizon may begin with a primary event timestamp (e.g., diagnosis timestamp) and terminate after a predetermined time period subsequent to the primary event timestamp (e.g., three months, six months, two years, or the like).

The term "patient profile" may refer to a data object storing and/or providing access to information/data associated with a patient/individual. The patient profile may also comprise member information/data, member features, and/or similar words used herein interchangeably that can be associated with a given member identifier for a patient/individual, claim, and/or the like. In some embodiments, member information/data can include age, gender, poverty rates, known health conditions, home location, profession, access to medical care, medical history, claim history, member identifier (ID), and/or the like. Member information/data may also include marital status, employment status, employment type, socioeconomic information/data (e.g., income information/data), relationship to the primary insured, insurance product information/data, insurance plan information/data, member classifications, language information/data, and/or the like.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware framework and/or operating system platform. A software component comprising assembly language instructions may require conversion into executable machine code by an assembler prior to execution by the hardware framework and/or platform. Another example programming language may be a higher-level programming language that may be portable across multiple frameworks. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM FRAMEWORK

FIG. 1 is a schematic diagram of an example system architecture 100 for performing predictive data analysis steps/operations and generating corresponding user interface data (e.g., for providing and/or updating a user interface). The system architecture 100 includes a risk determination system 101 comprising a risk determination computing entity 106 configured to generate predictive outputs that lead to performing one or more prediction-based actions. The risk determination system 101 may communicate with one or more external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The system architecture 100 includes a storage subsystem 108 configured to store at least a portion of the data utilized by the risk determination system 101. The risk determination computing entity 106 may be in communication with one or more external computing entities 102. The risk determination computing entity 106 may be configured to receive requests and/or data from external computing entities 102, process the requests and/or data to generate predictive outputs (e.g., predictive entity data objects), and provide the predictive outputs to the external computing entities 102. The external computing entity 102 (e.g., management computing entity) may periodically update/provide raw input data (e.g., predictive entity data objects) to the risk determination system 101. The external computing entities 102 may further generate user interface data (e.g., one or more data objects) corresponding to the predictive outputs and may provide (e.g., transmit, send and/or the like) the user interface data corresponding with the predictive outputs for presentation to user computing entities operated by end-users.

The storage subsystem 108 may be configured to store at least a portion of the data utilized by the risk determination computing entity 106 to perform predictive data analysis steps/operations and tasks. The storage subsystem 108 may be configured to store at least a portion of operational data and/or operational configuration data including operational instructions and parameters utilized by the risk determination computing entity 106 to perform predictive data analysis steps/operations in response to requests. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Risk Determination Computing Entity

FIG. 2 provides a schematic of a risk determination computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. Such functions, steps/operations, and/or processes may include, for example, transmitting, receiving, operating on, processing, displaying, storing, determining, creating/generating, monitoring, evaluating, comparing, and/or similar terms used herein interchangeably. In one embodiment, these functions, steps/operations, and/or processes can be performed on data, content, information, and/or similar terms used herein interchangeably.

As indicated, in one embodiment, the risk determination computing entity 106 may also include a network interface 220 for communicating with various computing entities, such as by communicating data, content, information, and/or similar terms used herein interchangeably that can be transmitted, received, operated on, processed, displayed, stored, and/or the like.

As depicted in FIG. 2, in one embodiment, the risk determination computing entity 106 may include or be in communication with a processing element 205 (also referred to as processors, processing circuitry, and/or similar terms used herein interchangeably) that communicates with other elements within the risk determination computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the risk determination computing entity 106 may further include or be in communication with non-volatile media (also referred to as non-volatile storage, memory, memory storage, memory circuitry and/or similar terms used herein interchangeably). In one embodiment, the non-volatile storage or memory may include at least one non-volatile memory 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the risk determination computing entity 106 may further include or be in communication with volatile media (also referred to as volatile storage, memory, memory storage, memory circuitry and/or similar terms used herein interchangeably). In one embodiment, the volatile storage or memory may also include at least one volatile memory 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the risk determination computing entity 106 with the assistance of the processing element 205 and operating system.

As indicated, in one embodiment, the risk determination computing entity 106 may also include a network interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the risk determination computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the risk determination computing entity 106 may include or be in communication with one or more input elements, such as a keyboard input, a mouse input, a touch screen/display input, motion input, movement input, audio input, pointing device input, joystick input, keypad input, and/or the like. The risk determination computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the risk determination computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the risk determination computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the risk determination computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the risk determination computing entity 106 and/or various other computing entities.

In another embodiment, the external computing entity 102 may include one or more components or functionality that are the same or similar to those of the risk determination computing entity 106, as described in greater detail above. As will be recognized, these frameworks and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

Described herein are various techniques for performing predictive data analysis steps/operations in relation to at least one predictive entity data object (e.g., a predictive entity data object that describes an entity with respect to which one or more predictive tasks/operations are performed). Some of the disclosed techniques may utilize one or more machine learning models to perform predictive data analysis steps/operations that lead to performing one or more prediction-based actions. Some of the described techniques utilize particular machine learning model(s) performing a particular set of steps/operations. However, a person of ordinary skill in the art will recognize that predictive data analysis steps/operations discussed herein may be performed using different combinations of machine learning model(s)/techniques than the particular combinations described herein.

FIG. 4 provides a flowchart diagram illustrating an example process 400 for determining a predicted risk measure for a predictive data entity and performing one or more prediction-based actions with respect to the predictive entity based at least in part on the predicted risk measure. As noted above, in some examples, the predictive entity may be a data object that describes a caregiver entity such as a member of a program associated with a health insurance insurer. The example predictive entity may correspond with a caregiver identifier (e.g., name, member ID, and/or the like). In some embodiments, the predictive entity may be associated with a recipient entity (e.g., care recipient entity). For instance, the caregiver entity may provide informal care to a care recipient entity and/or may be associated with the same membership or program of a health insurance provider.

Beginning at step/operation 402, the risk determination computing entity 106 identifies a risk determination machine learning model. In some embodiments, identifying the risk determination machine learning model may include generating the risk determination machine learning model. An example risk determination machine learning model may be configured to process hidden features of a predictive entity, e.g., a caregiver, in order to generate a predicted risk measure for the predictive entity. In particular, the risk determination machine learning model may be configured to generate a predicted risk measure with respect to a predictive entity for whom there is a limited amount of input data (e.g., medical claim entries). An example of a risk determination machine learning model is a trained supervised machine learning model (e.g., a trained supervised regression model, a convolutional neural network model, and/or the like).

Referring now to FIG. 5, a flowchart diagram illustrating an example process 500 for generating a risk determination machine learning model is provided.

Beginning at step/operation 502, the risk determination computing entity determines a primary event for each candidate predictive entity of a plurality of candidate predictive entities. The primary event for a candidate predictive entity may correspond with a record of an occurred event such as a diagnosis timestamp for a care recipient entity that is associated with the candidate predictive entity. The primary event may comprise a primary event code describing one or more medical claim attributes. By way of example, each primary event for a candidate predictive entity may be determined based at least in part on a diagnosis timestamp for a care recipient entity that is associated with the candidate predictive entity. In some embodiments, the primary event may correspond with a care recipient entity diagnosis that is associated with an increased or increasing predicted risk measure for an associated caregiver entity over a prediction time horizon. By way of example, a primary event may be a chronic long-term condition such as dementia, a neurodegenerative disease (e.g., Alzheimer's disease, Parkinson's disease, amyotrophic lateral sclerosis (ALS), multiple sclerosis (MS)), or the like. In some embodiments, the primary event may precipitate or lead to one or more medical claim entries, diagnoses and/or the like for a caregiver entity that is associated with the care recipient entity. In some embodiments, the risk determination computing entity 106 may identify/classify caregiver entities and care recipient entities from the plurality of candidate predictive entities. Additionally, the risk determination computing entity 106 may associate particular caregiver entities with particular care recipient entities (e.g., based at least in part on analysis of caregiver identifiers and care recipient identifiers). In one example, a caregiver and a care recipient that are associated with one another may share at least a portion of the described identifier information (e.g., a member identifier).

Subsequent to step/operation 502, the method 500 proceeds to step/operation 504. At step/operation 504, the risk determination computing entity 106 determines a prediction time horizon for each candidate predictive entity of the plurality of candidate predictive entities based at least in part on the primary event associated with the candidate predictive entity. In some embodiments, the candidate predictive entity may be associated with the prediction time horizon, a per-horizon historical claim set within the prediction time horizon, and a per-horizon claim count. In some embodiments, the per-horizon claim count may refer to a count of claims of a predictive entity (e.g., caregiver entity) occurring within a prediction time horizon. The prediction time horizon may be a time period following a primary event that begins with a primary event timestamp and terminates after a predefined time period (e.g., six months, a year, or the like) subsequent to the primary event timestamp. By way of example, the risk determination computing entity 106 may determine that a prediction time horizon associated with a caregiver entity begins with a diagnosis timestamp and terminates after a predefined time period following the diagnosis timestamp (e.g., one year after the diagnosis timestamp).

Subsequent to step/operation 504, the method 500 proceeds to step/operation 506. At step/operation 506, the risk determination computing entity 106 identifies a ground-truth subset of the plurality of candidate predictive entities based at least in part on each per-horizon claim count for a candidate predictive entity. The ground-truth subset may comprise one or more ground-truth predictive entities identified from the plurality of candidate predictive entities that are associated with per-horizon historical claim counts that satisfy a per-horizon claim count threshold. By way of example, an example per-horizon claim count threshold may be one hundred. In the above example, if a candidate predictive entity is associated with a per-horizon claim count threshold that is below one hundred counts, then the candidate predictive entity may be determined to not satisfy the per-horizon claim count threshold and thus the candidate predictive entity may be determined to be outside the ground-truth subset of predictive entities.

Subsequent to step/operation 506, the method 500 proceeds to step/operation 508. At step/operation 508, the risk determination computing entity 106 determines a ground-truth risk measure for each ground-truth predictive entity in the ground-truth subset. In some embodiments, the ground-truth risk measure may be a measure of risk that is determined based at least in part on a per-horizon claim set for the ground-truth predictive entity associated therewith. By way of example, the per-horizon claim set may be a count of claims, frequency of claims, combinations thereof, and/or the like, occurring within a prediction time horizon that satisfies a predetermined threshold (e.g., per-horizon claim count threshold). In some examples, the ground-truth risk measure may be determined based at least in part on a CCI score or other risk measure for a per-horizon claim set associated with the ground-truth predictive entity.

Subsequent to step/operation 508, the method 500 proceeds to step/operation 510. At step/operation 510, the risk determination computing entity 106 trains the risk determination machine learning model based at least in part on each ground-truth risk measure for a ground-truth predictive entity in the ground-truth subset. In some embodiments, training the risk determination machine learning model includes generating training data that is used to train the risk determination machine learning model. In some embodiments, training the risk determination machine learning model includes generating hidden features that serve as inputs to the risk determination machine learning model during training operations. As discussed herein, hidden features may include features or attributes that are associated with a predictive entity such as, for example, without limitation, member demographic information/data (e.g., age, gender, co-morbidities), claim frequency, claim type, claim value/amounts, number of hospitalizations, hospitalization time, duration of service, provider demographic information/data (e.g., specialty), diagnosis codes, procedure codes, facility, and/or the like. Additionally, the risk determination machine learning model may be generated based at least in part on one or more known attributes associated with an example predictive entity such as demographic information/data (e.g., age, geographic information) and the like. Accordingly, the risk determination machine learning model may utilize a combination of one or more hidden features and known attributes/features in order to generate a predictive output.

An operational example of a process 600 for training a risk determination machine learning model is depicted in FIG. 6. As depicted in FIG. 6, a risk determination machine learning model is identified and/or generated by identifying a selected subset of caregivers whose submitted claims satisfy a predetermined threshold claim count, which is an example of a per-horizon claim count threshold discussed above. The trained risk determination machine learning model then interpolates a ground-truth risk measure (e.g., a CCI score) across an entire population of predictive entities, including predictive entities outside of the ground-truth subset (e.g., for whom there is insufficient data or claim information). Subsequently, the trained risk determination machine learning model may be used to generate a predicted risk measure, which may be or comprise a CCI score, for all caregivers. Accordingly, certain caregivers that have a predicted risk measure or CCI score above a predetermined threshold can be identified as high-risk caregivers.

Returning to FIG. 4, subsequent to step/operation 402, the method 400 proceeds to step/operation 404. At step/operation 404, subsequent to identifying and/or generating the risk determination machine learning model, the risk determination computing entity 106 determines a predicted risk measure with respect to a predictive entity based at least in part on the risk determination machine learning model and one or more hidden features of the predictive entity. The predicted risk measure may be a predictive output that represents or describes an inferred measure of risk for the predictive entity. In some examples, the predictive entity may be a caregiver entity that is indirectly associated with a primary event such as a care recipient entity diagnosis. In some embodiments, the predicted risk measure may refer to a morbidity index defining an expected survival period and may include a CCI score or risk score.

Subsequent to step/operation 404, the method 400 proceeds to step/operation 406. At step/operation 406, subsequent to determining a predicted risk measure with respect to a predictive entity, the risk determination computing entity 106 performs one or more prediction-based actions based at least in part on the predicted risk measure.

Referring now to FIG. 7, an operational example 700 depicting a set of operations that are configured to perform one or more prediction-based actions is provided. As depicted in FIG. 7, the risk determination computing entity 106 is configured to process a caregiver entity at step/operation 702 and perform one or more prediction-based actions at step/operation 704.

As depicted in FIG. 7, generating a predicted risk score at step/operation 702 includes a plurality of sub-steps/sub-operations. As shown, generating a predicted risk score at step/operation 702 includes identifying a primary event at sub-step/sub-operation 702A. As depicted in FIG. 7, the primary event is associated with a diagnosis code (as shown, ICD 10 code G30 (Dementia)). Additionally, generating a predicted risk score includes identifying a caregiver entity at sub-step/sub-operation 702B. The caregiver entity may be associated with a care recipient entity that is in turn associated with the primary event. In some examples, as depicted, the caregiver entity may be associated with a caregiver identifier that is linked to or otherwise associated with a care recipient identifier. As further depicted in FIG. 7, generating a predicted risk score at step/operation 702 includes, at sub-step/sub-operation 702C, determining a predictive risk measure with respect to the caregiver entity (e.g., using a risk determination machine learning model). As noted above, the caregiver entity may be determined to be high-risk in an instance in which the predictive risk measure satisfies a predetermined threshold (e.g., is above the predetermined threshold).

As noted above, and as shown in FIG. 7, the risk determination computing entity 106 is configured to perform one or more prediction-based actions at step/operation 704. As illustrated in FIG. 7, performing one or more prediction-based actions at step/operation 704 includes scheduling a house call at sub-step/sub-operation 704A. Additionally, performing one or more prediction-based actions at step/operation 704 includes providing an alert to a clinician, such as a registered nurse, that is seeing or visiting the caregiver at sub-step/sub-operation 704B. As further depicted, performing one or more prediction-based actions includes providing caregiver information at sub-step/sub-operation 704C. This may include discussing health options with a caregiver (e.g., respite care, counselling, local services or the like). Additionally, providing caregiver information may include providing user interface data for presentation by a user computing entity as further discussed below.

In various embodiments, the risk determination computing entity 106 may be configured to respond to queries for and/or trigger generation (e.g., by an external computing entity 102) of user interface data (e.g., messages, data objects and/or the like) corresponding with predictive outputs. An external computing entity 102 may provide the user interface data for presentation by a user computing entity. The user interface data may correspond with an associated workflow and or one or more queues generated for presentation to an end user.

A queue may refer to an ordering of a plurality of data objects describing predictive entities (e.g., caregiver entities) and, in some examples, corresponding primary events and/or care recipient entities based at least in part on a portion of the predictive outputs described herein. In some embodiments, risk determination computing entity 106 may be configured to generate one or more API-based data objects corresponding with at least a portion of the predictive outputs and/or the one or more queues. The risk determination computing entity 106 may provide (e.g., transmit, send) the one or more API-based data objects representing at least a portion of the predictive outputs and/or the one or more queues to an end user interface (e.g., an investigation agent user interface) for display by a display device associated with the end-user interface, and/or for performing other computer-implemented actions. The predictive outputs may be used to dynamically update a user interface, or generate alerts for facilitating actions with respect to a healthcare services inventory (e.g., assigning portions of inventory or data subsets to a plurality of agents).

In some embodiments, performing the prediction-based actions at step/operation 406 comprises causing display of a prediction output user interface that describes data determined based at least in part on predicted risk measures for one or more predictive entities.

FIG. 8 provides an operational example showing a prediction output user interface 800 that may be generated based at least in part on user interface data which are in turn generated based at least in part on one or more predicted risk measures. The external computing entity 102 may generate the prediction output user interface 800 based at least in part on the user interface data and provide (e.g., transmitted, sent and/or the like) the prediction output user interface 800 for presentation by the prediction output user interface 800.

As depicted in FIG. 8, the prediction output user interface 800 may describe a care recipient entity and associated caregiver entity. In various embodiments, the prediction output user interface 800 may include one or more patient profiles (e.g., a care recipient patient profile and a caregiver patient profile). An example patient profile can be a data object storing and/or providing access to patient information/data. The patient record/profile may also comprise member information/data, patient features, and/or similar words used herein interchangeably that can be associated with a given member, claim, and/or the like. In some embodiments, patient information/data can include age, gender, poverty rates, known health conditions, home location, profession, access to medical care, medical history, claim history, patient identifier (ID), and/or the like. Patient information/data may also include marital status, employment status, employment type, socioeconomic information/data (e.g., income information/data), insurance product information/data, insurance plan information/data, member classifications, language information/data, and/or the like. Additionally, as depicted, the prediction output user interface 800 describes a risk score or predictive risk measure associated with the caregiver entity. As further depicted, the prediction output user interface 800 described a recommended action with respect to the caregiver entity. In some examples, the prediction output user interface 800 may display an alert or notification based at least in part on a recommended action to be taken.

The prediction output user interface 800 may also comprise messages to an end-user in the form of banners, headers, notifications, and/or the like. As will be recognized, the described elements are provided for illustrative purposes and are not to be construed as limiting the dynamically updatable interface in any way. A variety of other approaches and techniques can be used to adapt to various needs and circumstances.

Using the above-described techniques, various embodiments of the present invention disclose techniques for performing predictive data analysis steps/operations that are configured to generate a predicted risk measure for a predictive entity. These techniques are in turn configured to improve the efficiency of performing the noted predictive data analysis steps/operations and reliability of the generated results. Typically, predictive data analysis steps/operations require analysis of large amounts of data in order to accurately generate a predictive output. Accordingly, a predictive output may be inaccurate or unreliable in an instance in which insufficient amounts of data are available. Additionally, existing techniques are time consuming and require a lot of computational resources. There is a need for improved systems and methods that are configured to generate accurate predictive outputs in an efficient manner in an instance in which limited data and/or computing resources are available. Various embodiments of the present invention address that need by disclosing techniques for training risk determination machine learning models using per-horizon historical claim sets for ground-truth predictive entities whose per-horizon historical claim counts satisfy a per-horizon historical claim count threshold. The inventors have confirmed, via experiments and theoretical calculations, that various embodiments of the disclosed techniques improve efficiency and accuracy of predictive data analysis systems and predictive data analysis relative to various state-of-the-art solutions.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for generating a predicted risk measure for a first predictive entity, the computer-implemented method comprising:
   generating, using one or more processors, by utilizing a risk determination machine learning model and based at least in part on one or more hidden features of the first predictive entity, the predicted risk measure, wherein:
   (i) the risk determination machine learning model is generated based at least in part on a ground-truth risk measure for each ground-truth predictive entity in a ground-truth subset of a plurality of candidate predictive entities,
   (ii) the first predictive entity is among the plurality of candidate predictive entities but is outside of the ground-truth subset,
   (iii) each ground-truth predictive entity is associated with a prediction time horizon and a per-horizon historical claim set within the prediction time horizon,
   (iv) each per-horizon claim count of a per-horizon claim set for a ground-truth predictive entity satisfies a per-horizon claim count threshold,
   (v) each prediction time horizon for a ground-truth predictive entity is determined based at least in part on a primary event associated with the ground-truth predictive entity,
   (vi) each primary event for a ground-truth predictive entity is determined based at least in part on a diagnosis timestamp for a recipient entity associated with the ground-truth predictive entity, and
   (vii) each ground-truth risk measure for a ground-truth predictive entity is determined based at least in part on the per-horizon claim set for the ground-truth predictive entity; and
   initiating, using the one or more processors, the performance of one or more prediction-based actions based at least in part on the predicted risk measure.

2. The computer-implemented method of claim 1, wherein each ground-truth risk measure is determined based at least in part on a Charlson Comorbidity Index (CCI) score for the per-horizon claim set of the ground-truth predictive entity.

3. The computer-implemented method of claim 1, wherein the risk determination machine learning model comprises a trained supervised machine learning model.

4. The computer-implemented method of claim 3, wherein the trained supervised machine learning model comprises a trained supervised regression model.

5. The computer-implemented method of claim 1, wherein the one or more hidden features are generated based at least in part on one or more known attributes associated with the first predictive entity.

6. The computer-implemented method of claim 1, wherein each predictive entity of the plurality of candidate predictive entities corresponds to a caregiver identifier of a plurality of caregiver identifiers.

7. The computer-implemented method of claim 6, wherein each recipient entity for a predictive entity corresponds to a care recipient identifier for the caregiver identifier that is associated with the predictive entity.

8. A computing system for generating a predicted risk measure for a first predictive entity, the computing system comprising one or more processors and memory including program code, the memory and the program code configured to, with the one or more processors, cause the computing system to at least:
generate, using a risk determination machine learning model and based at least in part on one or more hidden features of the first predictive entity, the predicted risk measure, wherein:
(i) the risk determination machine learning model is generated based at least in part on a ground-truth risk measure for each ground-truth predictive entity in a ground-truth subset of a plurality of candidate predictive entities,
(ii) the first predictive entity is among the plurality of candidate predictive entities but is outside of the ground-truth subset,
(iii) each ground-truth predictive entity is associated with a prediction time horizon and a per-horizon historical claim set within the prediction time horizon,
(iv) each per-horizon claim count of a per-horizon claim set for a ground-truth predictive entity satisfies a per-horizon claim count threshold,
(v) each prediction time horizon fora ground-truth predictive entity is determined based at least in part on a primary event associated with the ground-truth predictive entity,
(vi) each primary event for a ground-truth predictive entity is determined based at least in part on a diagnosis timestamp for a recipient entity associated with the ground-truth predictive entity, and
(vii) each ground-truth risk measure for a ground-truth predictive entity is determined based at least in part on the per-horizon claim set for the ground-truth predictive entity; and
initiate the performance of one or more prediction-based actions based at least in part on the predicted risk measure.

9. The computing system of claim 8, wherein each ground-truth risk measure is determined based at least in part on a CCI score for the per-horizon claim set of the ground-truth predictive entity.

10. The computing system of claim 8, wherein the risk determination machine learning model comprises a trained supervised machine learning model.

11. The computing system of claim 10, wherein the trained supervised machine learning model comprises a trained supervised regression model.

12. The computing system of claim 8, wherein the one or more hidden features are generated based at least in part on one or more known attributes associated with the first predictive entity.

13. The computing system of claim 8, wherein each predictive entity of the plurality of candidate predictive entities corresponds to a caregiver identifier of a plurality of caregiver identifiers.

14. The computing system of claim 13, wherein each recipient entity for a predictive entity corresponds to a care recipient identifier for the caregiver identifier that is associated with the predictive entity.

15. A non-transitory computer-readable storage medium having computer-readable program code portions stored therein, the computer-readable program code portions configured to:
generate, using a risk determination machine learning model and based at least in part on one or more hidden features of the first predictive entity, the predicted risk measure, wherein:
(i) the risk determination machine learning model is generated based at least in part on a ground-truth risk measure for each ground-truth predictive entity in a ground-truth subset of a plurality of candidate predictive entities,
(ii) the first predictive entity is among the plurality of candidate predictive entities but is outside of the ground-truth subset,
(iii) each ground-truth predictive entity is associated with a prediction time horizon and a per-horizon historical claim set within the prediction time horizon,
(iv) each per-horizon claim count of a per-horizon claim set for a ground-truth predictive entity satisfies a per-horizon claim count threshold,
(v) each prediction time horizon fora ground-truth predictive entity is determined based at least in part on a primary event associated with the ground-truth predictive entity,
(vi) each primary event for a ground-truth predictive entity is determined based at least in part on a diagnosis timestamp for a recipient entity associated with the ground-truth predictive entity, and
(vii) each ground-truth risk measure for a ground-truth predictive entity is determined based at least in part on the per-horizon claim set for the ground-truth predictive entity; and
initiate the performance of one or more prediction-based actions based at least in part on the predicted risk measure.

16. The non-transitory computer-readable storage medium of claim 15, wherein each ground-truth risk measure is determined based at least in part on a CCI score for the per-horizon claim set of the ground-truth predictive entity.

17. The non-transitory computer-readable storage medium of claim 15, wherein the risk determination machine learning model comprises a trained supervised machine learning model.

18. The non-transitory computer-readable storage medium of claim 17, wherein the trained supervised machine learning model comprises a trained supervised regression model.

19. The non-transitory computer-readable storage medium of claim 15, wherein the one or more hidden features are generated based at least in part on one or more known attributes associated with the first predictive entity.

20. The non-transitory computer-readable storage medium of claim 15, wherein each predictive entity of the plurality of candidate predictive entities corresponds to a caregiver identifier of a plurality of caregiver identifiers.

* * * * *

UNITED STATES PATENT AND TRADEMARK OFFICE
CERTIFICATE OF CORRECTION

| | | |
|---|---|---|
| PATENT NO. | : 11,955,244 B2 | Page 1 of 1 |
| APPLICATION NO. | : 17/305273 | |
| DATED | : April 9, 2024 | |
| INVENTOR(S) | : Conor Breen et al. | |

It is certified that error appears in the above-identified patent and that said Letters Patent is hereby corrected as shown below:

On the Title Page

In Column 1, item (72), Inventors, Line 2, delete "MacManus," and insert -- Mac Manus, --, therefor.

In the Claims

In Column 21, Line 39, Claim 8, delete "fora" and insert -- for a --, therefor.

In Column 22, Line 34, Claim 15, delete "fora" and insert -- for a --, therefor.

Signed and Sealed this
Third Day of September, 2024

Katherine Kelly Vidal
*Director of the United States Patent and Trademark Office*